United States Patent [19]

Osman et al.

[11] 4,361,494
[45] Nov. 30, 1982

[54] ANISOTROPIC CYCLOHEXYL CYCLOHEXYLMETHYL ETHERS

[75] Inventors: Maged A. Osman, Zurich; Laszlo Revesz, Basel, both of Switzerland

[73] Assignee: BBC Brown, Boveri, & Company, Limited, Baden, Switzerland

[21] Appl. No.: 217,138

[22] Filed: Dec. 17, 1980

[30] Foreign Application Priority Data

Dec. 17, 1979 [CH] Switzerland ............ 11139/79

[51] Int. Cl.³ .............. C09K 3/34; G02F 1/13; C07C 43/184; C07C 43/21; C07C 93/12; C07C 121/46
[52] U.S. Cl. ............ 252/299.63; 252/299.5; 260/464; 260/465 D; 260/465 E; 260/465 F; 260/465 R; 560/1; 560/19; 560/20; 560/49; 560/73; 560/107; 560/125; 560/126; 568/583; 568/586; 568/644; 568/645; 568/631; 568/659; 568/660; 568/661; 568/664; 564/443
[58] Field of Search ........... 252/299.63, 299.6, 299.66, 252/299.67, 299.5, 299.64, 299.65; 560/1, 19, 20, 49, 73, 107, 125, 126; 568/586, 583, 644, 645, 631, 659, 660, 661, 664; 260/464, 465 D, 465 E, 465 F, 465 R, 576, 563 R, 563 C

[56] References Cited

U.S. PATENT DOCUMENTS

| | | | |
|---|---|---|---|
| 4,035,056 | 7/1977 | Coates et al. | 252/299.66 |
| 4,212,762 | 7/1980 | Dubois et al. | 252/299.64 |
| 4,228,029 | 10/1980 | Osman | 252/299.63 |
| 4,229,315 | 10/1980 | Krause et al. | 252/299.63 |
| 4,261,651 | 4/1981 | Gray et al. | 252/299.63 |

OTHER PUBLICATIONS

Carr, N., et al., Mol. Cryst. Liq. Cryst., vol. 66, p. 267 (1981).
Gray, G. W., et al., Mol. Cryst. Liq. Cryst., vol. 53, pp. 147-166 (1979).
Deutscher, H. J., et al., Advances in Liq. Cryst. Res. and Appls., pp. 1075-1079, Proceedings of the Third Liq. Cryst. Conf. of Bata, L., vol. 2, Socialist Countries, Budapest, Aug. 27-31, 1979, Pergamon Pr. (1980).
Osman, M. A., et al., Mol. Cryst. Liq. Cryst., vol. 72 (Letters) pp. 89-94 (1981).
Osman, M. A., et al., Mol. Cryst. Liq. Cryst., vol. 56 (Letters), pp. 105-109 (1979).

Primary Examiner—Teddy S. Gron
Attorney, Agent, or Firm—Oblon, Fisher, Spivak, McClelland & Maier

[57] ABSTRACT

New anisotropic compounds suitable for use in LC-display devices are disclosed and claimed. The new compounds are cyclohexyl cyclohexylmethyl ethers of formula (1):

$$X-\boxed{\text{H trans}}-CH_2O-\boxed{\text{H trans}}-Y \qquad (1)$$

in which X and Y are respectively hydrogen, alkyl group with 1 to 12 C-atoms, alkoxy group with 1 to 12 C-atoms, monoalkylamino group with 1 to 12 C-atoms, nitrile group, nitro group, halogen, or cyclic radical of formula (1a) or (1b):

$$R^1-\boxed{\phantom{x}}-Z^1- \qquad R^2-\boxed{\text{H trans}}-Z^2-$$

(1a)       (1b)

in which $R^1$ and $R^2$ represent hydrogen alkyl group with 1 to 12 C-atoms, alkoxy group with 1 to 12 C-atoms, monoalkylamino group with 1 to 12 C-atoms, nitrile group, nitro group or halogen, and $Z^1$ and $Z^2$ represent simple covalent bonds or grounds of the formulas —COO—, —OOC—, —CH$_2$O— or —OCH$_2$, with the requirement that only one of the groups X, Y can be a cyclicradical or formula (1a) or (1b). Also disclosed and claimed are LC-mixtures containing these compounds and methods for their synthesis.

14 Claims, No Drawings

ANISOTROPIC CYCLOHEXYL CYCLOHEXYLMETHYL ETHERS

BACKGROUND OF THE INVENTION

1. Field of the Invention

The present invention relates to new anisotropic compounds, i.e. a new class of cyclohexyl cyclohexylmethyl ethers, as well as to liquid crystal (LC) mixtures containing the cyclohexyl cyclohexylmethyl ethers used as the dielectric medium for liquid crystal displays. The invention further relates to a method of producing the new anisotropic compounds.

2. Description of the Prior Art

Anisotropic biphenyl compounds of the formula (10):

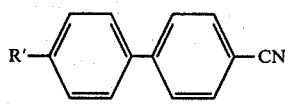

in which $R^1$ means an alkyl radical, for example, are known from the German Offenlegungsschrift No. 2,356,085 and are among the substances most commonly used for LC-mixtures.

Furthermore, it is known from the German Offenlegungsschrift No. 2,636,684 that the relatively high viscosity and optical anisotropy ($\Delta n$) of the compounds of formula (10) can be reduced by substituting a trans-1,4-cyclohexylene ring for a phenylene ring, which leads to phenylcyclohexanes of the formula (20):

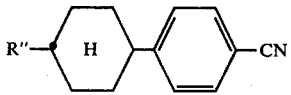

in which $R''$ has the same meaning as $R'$ in formula (10).

The $\Delta n$ values of anisotropic components of LC-mixtures customarily represent a measurement of the optical anisotrophy and are expressed as the difference, $\Delta n = n_{\parallel} - n_{\perp}$, of the refracting indices parallel or perpendicular, respectively, to the molecular axis of the substance being considered.

For many types of LC-displays, particularly the so-called "guest-host" effect cells, nematic LC-phases with as small $\Delta n$-values as possible, e.g., not more than 0.1, are needed. By replacing one phenylene ring in compounds of formula (10) with a trans-cyclohexylene ring, the $\Delta n$-value is practically reduced by one-half ($\Delta n \approx 0.22$ with compounds of formula (10), n 0.12 with compounds of formula (20)).

If the second phenylene ring of the anisotropic compounds of formula (10) or the remaining phenylene ring of the compounds of formula (20) is replaced by a cyclohexylene ring, one arrives at the cyclohexylcyclohexanes of formula (30) known from the German Offenlegungsschrift No. 2,702,598,

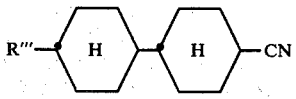

in which $R''$ has the same meaning as that given for $R'$ in formula (10); also, the $\Delta n$-value is thereby reduced to values less than 0.1, typically to ca. $\Delta n = 0.06$.

The disadvantage, however, with the compounds of formula (30) is that hydrogenation of the second phenylene ring causes a definite tendency toward forming smectic phases (see R. Pohl et al, Phys. Letter, 65A (2), 169(1978)).

The applicant suggested in the Swiss patent application No. 6672/79 (also see M. A. Osman and L. Revesz, Mol. Cryst. and Liqu. Cryst., 56 105(1979)) a new compound class, namely cyclohexyl cyclohexanoates of formula (40):

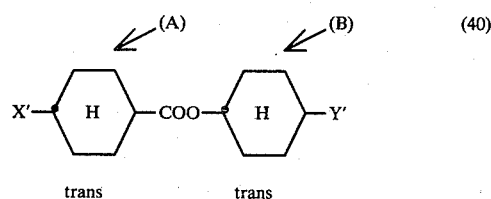

in which $X'$ and $Y'$ independently represent hydrogen, alkyl group with 1 to 12 C-atoms, alkoxy group with 1 to 12 C-atoms, monoalkylamino group with 1 to 12 C-atoms, halogen, nitrite (—CN), nitro, or para substituted cyclic radical, e.g., a phenyl, cyclohexyl, piperidine or pyrrolidine ring that is connected by way of a simple covalent bond, a carboxyl, or oxycarbonyl group with the cyclohexyl rings (A) and (B) of the basic skeleton of formula (40), with the requirement that only one of the groups $X'$, $Y'$ means a cyclic radical.

The anisotropic compounds of formula (40) have advantageously low $\Delta n$-values, chiefly less than 0.1, and, in contrast to the known compounds of formula (30), have no definite tendency to form smectic phases. However, the carboxyl group forming the bridge between cyclohexyl rings (A) and (B) of compounds of formula (40) is relatively reactive and sensitive to hydrolysis.

SUMMARY OF THE INVENTION

Accordingly, one object of the present invention is to provide new anisotropic compounds offering the advantages of the cyclohexyl cyclohexaneoates of formula (40) having, in comparison to these however, a higher chemical stability.

It is also an object of this invention to provide LC-mixtures which contain anisotropic compounds, and to provide methods of producing said anisotropic compounds.

These and other objects as will hereinafter be recognized from the ensuing discussions have been attained by providing anisotropic compounds in the form of cyclohexylcyclohexylmethyl ether compounds of formula (1):

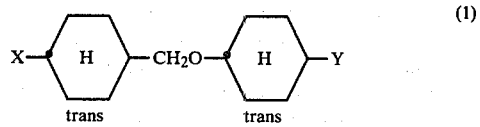

in which X and Y independently represent hydrogen, alkyl group with 1 to 12 C-atoms, alkoxy group with 1 to 12 C-atoms, monoalkylamino groups with 1 to 12

C-atoms, nitrile, nitro, halogen, or cyclic radical of formula (1a) or (1b):

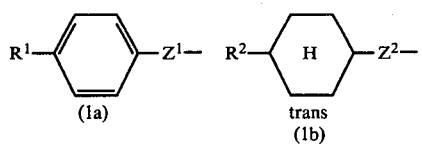

in which $R^1$ and $R^2$ represents hydrogen, alkyl group with 1 to 12 C-atoms, alkoxy group with 1 to 12 C-atoms, monoalkylamino group with 1 to 12 C-atoms, nitrile group, nitro group, or halogen atoms and $Z^1$ and $Z^2$ represent simple covalent bonds or groups of formulas —COO—, —CH$_2$O— or —OCH$_2$—, with the requirement that only one of the groups X, Y represents a cyclic, radical of formula (1a) or (1b).

The compounds of formula (1) are suited for liquid crystal mixtures for use in operating displays with a nematic phase, either in mixtures with one another or together with other known compounds.

DETAILED DESCRIPTION OF THE INVENTION

It was discovered that the objects of the invention can be achieved by replacing the carboxyl group which joins cyclohexyl rings (A) and (B) of compounds (40) with an ether bridge of the formula —CH$_2$O—. Surprisingly, i.e. contrary to expectations based on prior art teachings, the ethers generally have lower melting points than the corresponding carboxyl compounds (40).

The new anisotropic compounds according to the present invention have the formula (1):

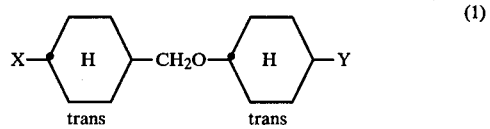

in which X and Y independently represent hydrogen, alkyl group with 1 to 12 C-atoms, alkoxy group with 1 to 12 C-atoms, monoalkylamino group with 1 to 12 C-atoms, nitrile group, nitro group, halogen, or cyclic radical of the formula (1a) or (1b):

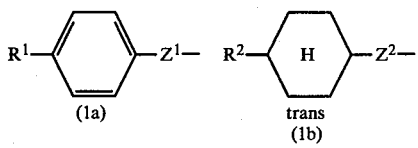

in which $R^1$ and $R^2$ represent hydrogen, alkyl group with 1 to 12 C-atoms, alkoxy group with 1 to 12 C-atoms, monoalkylamino group with 1 to 12 C-atoms, nitrile group, nitro group, or halogen, and $Z^1$ and $Z^2$ represent simple covalent bonds or groups of the formulas —COO—, —OOC—, —CH$_2$O— or —OCH$_2$—, with the requirement that only one of the groups X, Y may represent a cyclic radical of formulas (1a) or (1b).

The alkyl part in the alkyl-, alkoxy- or N-monoalkylamino-radicals of X, Y, $R^1$ or $R^2$ is preferably straight chained; alkyl parts with 3 to 10 C-atoms, and particularly alkyl parts with 3 to 8 C-atoms, are preferred here. Cl and Br are usually preferred as the halogen for X, Y, $R^1$ or $R^2$. In addition, compounds (1) are often preferred in which X is not equal to Y.

With the new anisotropic compounds, LC-mixtures can be produced which comprise predominantly or nearly completely (e.g., up to 90% by weight) compounds of formula (1) mixed together, or which contain at least one compound of formula (1) as a component, e.g. in a ratio of 2 to 40% by weight based on the LC-mixture, e.g., with known anisotropic compounds and/or other components suitable for LC-mixtures.

The new anisotropic compounds (1), or the LC-mixtures produced with them, are generally suited for nematic phases with small optical anisotrophy and low viscosity; if the LC-mixtures or the compounds of formula (1) formed according to the present invention have a positive dielectric anisotrophy, the nematic phases are particularly suited for known LC-displays in the form of rotating cells in multiplex operation as well as for known LC-displays functioning on the so-called "guest-host" effect. If the LC-mixture according to the invention or the invented compounds of formula (1) have a negative dielectric anisotrophy, the nematic phases formed with them are particularly suited for known LC-displays operating according to the inverse guest-host effect, functioning as dynamic dispersion cells, or as so-called DDM-cells.

The new compounds (1) can be obtained by reducing the corresponding cyclohexyl cyclohexanoates, which are, among other ways obtainable according to the literature reference given above, i.e.:

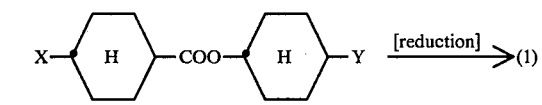

wherein X and Y have the meaning given above. One method of achieving this conversion is with the aid of BF$_3$/NaBH$_4$ according to known methods for the reductive conversion of ester into ether (see, e.g., G. R. Pettit and D. M. Piatate, *J. Org. Chem.* 27 2127 (1962)).

In addition, the new compounds (1) can also be obtained by condensation or etherification of a corresponding p-X-trans-cyclohexylmethyl compound of formula (3a), with a corresponding p-Y-trans cyclohexyloxy compound of formula (3b), i.e.:

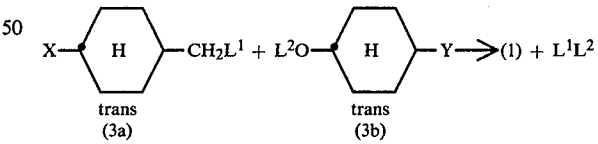

wherein X and Y have the meaning given above and $L^1$ and $L^2$ are original groups or original atoms that become bonded together in the condensation of $L^1L^2$. If $L^1$ is a halogen, for example, such as Br, the condensation can take place with $L^2$=H while forming hydrogen halide as a byproduct. The hydrogen halide can be combined in the usual manner with an organic substance, e.g. pyridine, or an inorganic substance, e.g. sodium carbonate, to promote the reaction.

A method suitable for producing the new compounds (1) by condensation or etherification is described by G. W. Gray and D. G. McDonnell in *Mol. Cryst. Liqu. Cryst.*, 53, 147–166, (1979). This reference describes the formation of cyclohexylmethyl ethers with an aromatic (phenylene, biphenylene or naphthylene) ring on the ether oxygen, i.e., compounds of formula (50).

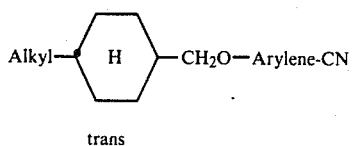

trans (50)

These have, however, generally higher melting points than the corresponding carboxyl compounds of formula (60).

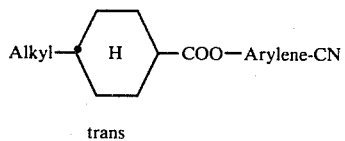

trans (60)

Surprisingly, the ethers of formula (1) according to the invention have generally lower melting points than the corresponding cyclohexyl cyclohexanoates of formula (40).

Compounds (3a) and (3b), which are required for the synthesis of the compounds of formula (1), are known or can be produced in a manner similar to that used to produce known compounds. Examples of the synthesis of these starting materials are given below.

The above disclosure generally describes the present invention. A more complete understanding can be obtained by reference to the following specific examples, which are provided herein for purposes of illustration only and are not intended to be limiting unless otherwise specified.

EXAMPLE 1

Production of trans-4-phenylcyclohexyl trans-4'-n-propylcyclohexylmethyl ether (11)

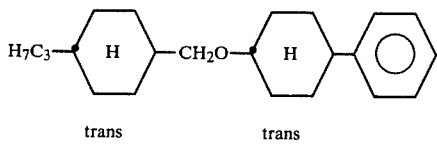

(11)

While being chilled with ice, 0.8 g (0.021 mole) of NaBH₄ were placed in 70 ml of diethylene glycol dimethyl ether and simultaneously reacted with 4.5 g (0.0137 mole) of trans-4-phenylcyclohexyl trans-4'-n-propylcyclohexanoate in 75 ml of tetrahydrofurane or in a solution of 37 ml (0.29 mole) of boron trifluoride etherate in 75 ml of tetrahydrofurane, during which time the temperature was not allowed to exceed 5° C. After this addition was completed the reaction mixture was brought to room temperature and heated for 1 hour at reflux. Processing was began by adding 100 ml of 2 N HCl and distilling away the organic solvents. The aqueous phase was extracted three times with methylene chloride; the combined organic phase was washed with a NaCl solution, dried with Na₂SO₄, and concentrated. The crystalline raw product was chromatographed on silica gel and recrystallized from ethanol. $T_k$ 50.5° C., $T_c$ (22° C.).

The $T_k$-value of the corresponding cyclohexyl cyclohexanoate compound (40), in contrast, is 84.4° C., the $T_c$-value, (69.5° C.). As is customary, $T_k$ here means the transition temperature from the crystalline to the liquid phase and $T_c$ the clarification temperature. A $T_c$-value given in parentheses means a measurement in the sub-cooled state.

EXAMPLE 2

Production of trans-(4''-n-pentyl)-4'-phenylcyclohexylmethyl-trans-4-n-propylcyclohexyl ether(12)

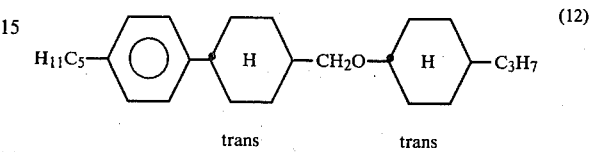

(12)

NaBH₄ (0.8 g, 0.021 mole) was added, while being ice chilled, to 70 ml of diethyleneglycoldimethyl ether and simultaneously reacted with 5.5 g (0.0137 mole) of trans-4-n-propylcyclohexyl trans-(4''-n-pentyl)-4'-phenylcyclohexanoate in 75 ml of tetrahydrofurane or a solution of 3.7 ml (0.29 mole) of boron trifluoroeitherate in 75 ml of tetrahydrofurane, during which time the temperature was not allowed to exceed 5° C. After this addition was completed the reaction mixture was brought to room temperature and heated for 1 hour at reflux. Processing was begun by adding 100 ml of 2 N HCl and distilling away the organic solvents. The aqueous phase was extracted three times with methylene chloride; the combined organic phase was washed with NaCl solution, dried with Na₂SO₄, and concentrated. The product, the compound (12), was purified chromatographically with silica gel and recrystallized from ethanol. $T_c$ 87.7° C.

Compound (12) showed a definite tendency to form sub-cooled melts and is not frozen down to 0° C. In contrast the corresponding cyclohexyl cyclohexanoate exhibits a $T_k$-value of 84.2° C. and a $T_c$-value of 177.3° C.

EXAMPLE 3

The compound of formula (11) produced in accordance with Example 1 by reduction of the corresponding cyclohexylcyclohexanoate was also produced by condensation, or etherization, of corresponding compounds of formulas (3a) and (3b). The process was carried out as follows:

(A) Production of trans-4-n-propylcyclohexylmethanol of formula (31)

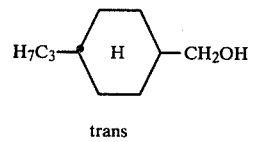

(31)

Trans-4-n-propylcyclohexane carboxylic acid (23.8 g, 0.14 mole), was dissolved in 150 ml of dry ether and added dropwise with stirring into a suspension of 11.4 g (0.3 mole) of LiAlH₄ in 300 ml of ether. After the addition the mixture was heated for 2 hours at reflux, and then the supernatant LiAlH₄ was decomposed with water while being cooled. The reaction mixture was then poured onto 20% hydrochloric acid and stirred until the inorganic salts dissolved. The product of formula (31) was extracted with diethyl ether; the combined organic phases were washed with water, dried with MgSO4 and concentrated.

(B) Production of trans-4-n-propylcyclohexylmethyl bromide (32)

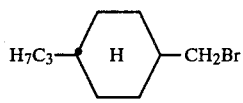

Compound (31) obtained according to section (A) (15.6 g, 0.1 mole) was added at 0° C. to 150 ml of pyridine-benzene mixture (1:1), and while being stirred, the solution was added to 9.0 g (0.033 mole) of PBr3. The reaction mixture was stirred for 2 hours at 0° C. and then 2 hours at room temperature, poured over ice/2 N HCl and extracted with diethyl ether. The ether extract was washed once each with 2 N HCl, 2 N NaOH, and NaCl solution, dried with Na2SO4, and concentrated. The bromide of formula (32) was purified chromatographically with silica gel.

(C). Production of Compound (11) by etherification

NaH (1.56 g, 0.065 mole) in 30 ml of dry tetrahydrofurane (THF) was slowly added to 11.4 g (0.065 mole) of trans-4-phenylcyclohexanol in 20 ml THF while controlling the evolution of hydrogen, and the resulting mixture was stirred overnight at room temperature. Bromide of formula (32), obtained in accordance with section (B) above, (14.2 g, 0.065 mode) was dissolved in 20 ml of THF, and the resulting solution was added dropwise to the mixture. The entire resulting mixture was heated for 2 hours at reflux. Processing began with distilling off the THF. The residue was poured into ice water and extracted with diethyl ether; the ether phases were washed with NaCl solution, dried with Na2SO4 and concentrated. The raw product of formula (11) was purified on silica gel and recrystallized from ethanol. $T_k$ 50.5° C., $T_c$ (22° C.).

EXAMPLE 4

The compound of formula (12) produced according to Example 2 by reduction of the corresponding cyclohexyl chclohexanoate was also produced by condensation or etherification of corresponding compounds of formulas (3a) and (3b). The process was carried out as follows:

(A) Production of trans-(4'-n-pentyl)-4-phenylcyclohexylmethanol of formula (33)

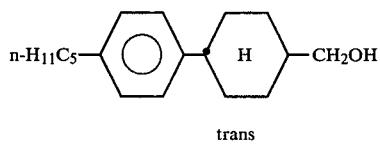

Trans-(4'-n-pentyl)-4-phenylcyclohexane carboxylic acid (38.3 g, 0.14 mole) was dissolved in 150 ml of dry diethyl ether and added dropwise into a suspension of 11.4 g (0.3 mole) LiAlH4 in 300 ml of ether while stirring. After this addition, the mixture was heated for 2 hours at reflux and then, while being cooled, the supernatant LiAlH4 was decomposed with water. The reaction mixture was then poured onto 20% hydrochloric acid and stirred until the inorganic salts dissolved. The product was extracted with diethyl ether; the ether phases were washed with water, dried with MgSO4, and concentrated.

(B) Production of trans-(4'-n-pentyl)-4-phenylcyclohexylmethyl bromide of formula (34)

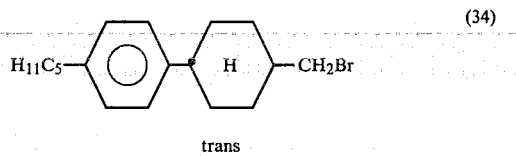

Compound (33), obtained according to section (A), (26.0 g, 0.1 mole) in 150 ml of pyridine-benzene mixture (1:1) at 0° C. was added dropwise; with stirring into 9.0 g (0.033 mole) of PBr3. The reaction mixture was stirred for 2 hours at 0° C. and then for 2 hours at reflux, poured over ice/2 N HCl and extracted with diethyl ether. The ether extracts were washed once each with 2 N HCl, 2 N NaOH, and NaCl solution, dried with Na2SO4, and concentrated. The bromide (34) was purified chromatographically with silica gel and recrystallized from ethanol.

(C) Production of the compound (12) by etherification

NaH (1.56 g, 0.065 mole) in 30 ml of dry THF was slowly mixed with 9.23 g (0.065 mole) of trans-4-n-propylcyclohexanol in 20 ml of THF while regulating the evolution of hydrogen, and the resulting mixture was stirred overnight at room temperature. Compound (34) (21 g, 0.065 mole), obtained according to section B, in 20 ml THF, was added dropwise, and the entire amount was heated for 2 hours at reflux. The processing was begun by distilling off the THF. The residue was poured into ice water and extracted with diethyl ether. The ether phases were washed with NaCl solution, dried with Na2SO4 and concentrated. The raw product was purified with silica gel and recrystallized from ethanol. The physical date of the resulting compound (12) are given in Example 2.

EXAMPLES 5-73

The following anisotropic compounds of formula (1) can also be obtained in a manner similar to those in Examples 1-4:

Ex.

5: trans-4-phenylcyclohexyl trans-4'-n-propylcyclohexylmethyl ether
6: trans-4-phenylcyclohexyl trans-4'-n-pentylcyclohexylmethyl ether
7: trans-4-phenylcyclohexyl trans-4'-n-heptylcyclohexylmethyl ether
8: trans-4-phenylcyclohexyl trans-4'-n-nonylcyclohexylmethyl ether
9: trans-(4''-n-propyl)-4'-phenylcyclohexylmethyl trans-4-n-propylcyclohexyl ether
10: trans-(4''-n-pentyl)-4'-phenylcyclohexylmethyl trans-4-n-propylcyclohexyl ether 11: trans-(4''-n-heptyl)-4'-phenylcyclohexylmethyl trans-4-n-propylcyclohexyl ether
12: trans-(4''-n-nonyl)-4'-phenylcyclohexylmethyl trans-4-n-propylcyclohexyl ether
13: trans-(4''-n-propyl)-4'-phenylcyclohexylmethyl trans-4-n-pentylcyclohexyl ether
14: trans-(4''-n-propyl)-4'-phenylcyclohexylmethyl trans-4-n-heptylcyclohexyl ether
15: trans-(4''-n-propyl)-4'-phenylcyclohexylmethyl trans-4-n-nonylcyclohexyl ether
16: trans-(4''-n-pentyl)-4'-phenylcyclohexylmethyl trans-4-n-pentylchcyclohexyl ether
17: trans-(4''-n-pentyl)-4'-phenylchcyclohexylmethyl trans-4-n-heptylcyclohexyl ether
18: trans-(4''-n-pentyl)-4'-phenylcyclohexylmethyl trans-4-n-nonylcyclohexyl ether
19: trans-(4''-n-heptyl)-4'-phenylcyclohexylmethyl trans-4-n pentylcyclohexyl ether
20: trans-(4''-n-heptyl)-4'-phenylcyclohexylmethyl trans-4-n-heptylcyclohexyl ether
21: trans-(4''-n-heptyl)-4'-phenylcyclohexylmethyl trans-4-n-nonylcyclohexyl ether
22: trans-(4''-n-nonyl)-4'-phenylcyclohexylmethyl trans-4-n-pentylcyclohexyl ether
23: trans-(4''-n-nonyl)-4'-phenylcyclohexylmethyl trans-4-n-heptylcyclohexyl ether
24: trans-(4''-(n-nonyl)-4'-phenylcyclohexylmethyl trans-4-n-nonylcyclohexyl ether
25: trans-4'-methylcyclohexylmethyl trans-4-n-propylcyclohexyl ether
26: trans-4'-n-propylcyclohexylmethyl trans-4-n-propylcyclohexyl ether
27: trans-4'-n pentylcyclohexylmethyl trans-4-n-propylcyclohexyl ether
28: trans-4'-n-heptylcyclohexylmethyl trans-4-n-propylcyclohexyl ether
29: trans-4'-n nonylcyclohexylmethyl trans-4-n-propylcyclohexyl ether
30: trans-4'-n propylcyclohexylmethyl trans-4-methylcyclohexyl ether
31: trans-4'-n-propylcyclohexylmethyl trans-4-n-pentylcyclohexyl ether
32: trans-4'-n-propylcyclohexylmethyl trans-4-n heptylcyclohexyl ether
33: trans-4'-n-propylcyclohexylmethyl trans-4-n-nonylcyclohexyl ether
34: trans-4'-methylcyclohexylmethyl trans-4-n-pentylcyclohexyl ether
35: trans-4'-n-pentylcyclohexylmethyl trans-4-n-pentylcyclohexyl ether
36: trans-4'-n-heptylcyclohexylmethyl trans-4-n-pentylcyclohexyl ether
37: trans-4'-n-nonylcyclohexylmethyl trans-4-n-pentylcyclohexyl ether
38: trans-4'-n-pentylcyclohexylmethyl trans-4-methylcyclohexyl ether
39: trans-4'-n-pentylcyclohexylmethyl trans-4-n-heptylcyclohexyl ether
40: trans-4'-n-pentylcyclohexylmethyl trans-4-n-nonylcyclohexyl ether
41: trans-4'-methylcyclohexylmethyl trans-4-n-heptylcyclohexyl ether
42: trans-4'-n-heptylcyclohexylmethyl trans-4-n-heptylcyclohexyl ether
43: trans-4'-n-nonylcyclohexylmethyl trans-4-n-heptylcyclohexyl ether
44: trans-4'-n-heptylcyclohexylmethyl trans-4-methylcyclohexyl ether
45: trans-4'-n-heptylcyclohexylmethyl trans-4-n-nonylcyclohexyl ether
46: trans-4'-methylcyclohexylmethyl trans-4-n-nonylcyclohexyl ether
47: trans-4'-n-nonylcyclohexylmethyl trans-4-n-nonylcyclohexyl ether
48: trans-4'-n-nonylcyclohexylmethyl trans-4-methylcyclohexyl ether
49: trans-4'-phenylcyclohexyl trans-4-ethoxycyclohexylmethyl ether
50: trans-4'-phenylcyclohexyl trans-4-n-butyloxycyclohexylmethyl ether
51: trans-4'-phenylcyclohexyl trans-4-n-hexyloxycyclohexylmethyl ether
52: trans-4'-phenylcyclohexyl trans-4-n-octyloxycyclohexylmethyl ether
53: trans-(4''-ethoxy)-4'-phenylcyclohexylmethyl trans-4-n-propylcyclohexyl ether
54: trans-(4''-n-butyloxy)-4'-phenylcyclohexylmethyl trans-4-n-propylcyclohexyl ether
55: trans-(4''-n-hexyloxy)-4'-phenylcyclohexylmethyl trans-4-n-propylcyclohexyl ether
56: trans (4''-n-octyloxy)-4'-phenylcyclohexylmethyl trans-4-n-propylcyclohexyl ether
57: trans-(4''-ethoxy)-4'-phenylcyclohexylmethyl trans-4-n-phenylcyclohexyl ether
58: trans-(4''-n-butyloxy)-4'-phenylcyclohexylmethyl trans-4-n-pentylcyclohexyl ether
59: trans-(4''-n-hexyloxy)-4'-phenylcyclohexylmethyl trans-4-n-pentylcyclohexyl ether
60: trans-(4''-n-octyloxy)-4'-phenylcyclohexylmethyl trans-4-n-pentylcyclohexyl ether
61: trans-4'-n-propylcyclohexylmethyl trans-4-n-pentylaminocyclohexyl ether
62: trans-4'-n-propylaminocyclohexylmethyl trans-4-n-pentylcyclohexyl ether
63: trans-4'-n-heptylaminocyclohexylmethyl trans-4-n-propylcyclohexyl ether
64: trans-4'-cyanocyclohexylmethyl trans-4-n-heptylcyclohexyl ether
65: trans-4'-n-heptylcyclohexylmethyl trans-4-cyanocyclohexyl ether
66: trans-4'-n-pentyl-4-bicyclohexyl trans-4''-n-propylcyclohexylmethyl ether
67: trans-4'-n-propyl-4-bicyclohexyl trans-4''-n-pentylcyclohexylmethyl ether
68: trans-4'-cyano-4-bicyclohexyl trans-4''-n-heptylcyclohexylmethyl ether
69: trans-4'-n-pentyl-4-bicyclohexyl trans-4''-cyanocyclohexylmethyl ether
70: trans-4-n-propylcyclohexylmethyl trans-4'-[(trans-4''-n-pentyl)-cyclohexyloxymethyl]cyclohexyl ether
71: trans-4-n-pentylcyclohexylmethyl trans-4'-[(trans-4''-n-propyl)cyclohexyloxymethyl]cyclohexyl ether
72: trans-4-n-heptylcyclohexylmethyl trans-4'-[(trans-4''-n-heptyl)cyclohexyloxymethyl]cyclohexyl ether
73: trans-4-n-heptylcyclohexylmethyl trans-4'-[(trans-4''-cyano)cyclohexyloxymethyl]cyclohexyl ether Of course, the new anisotropic compounds of formula (1) have an extraordinarily broad spectrum of uses, due, among other thngs, to their low optical anisotrophy and their comparatively low viscosity. Depending on the choice of substituents X, Y in formula (1), in the sense of choosing a stronger or weaker polarization of the molecule, the new anisotropic compounds (1) can carry out varying functions in LC-mixtures of the types named above; thus, completely different LC-mixtures can be formed with the anisotropic compounds (1),

We claim:

1. Anisotropic compounds of formula (1):

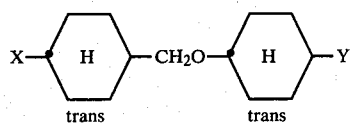 (1)

in which X and Y independently represent hydrogen, an alkyl group with 1 to 12 C-atoms, an alkoxy group with 1 to 12 C-atoms, a monoalkylamino group with 1 to 12 C-atoms, a nitrile group, a nitro group, halogen, or a cyclic radical of formula (a) or (b):

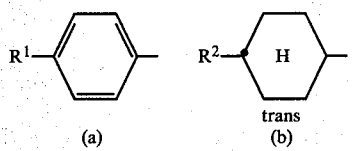

in which $R^1$ and $R^2$ independently represent hydrogen, an alkyl group with 1 to 12 C-atoms, an alkoxy group with 1 to 12 C-atoms, a monalkylamino group with 1 to 12 C-atoms, a nitrile group, a nitro group, or halogen, with the proviso that only one of the groups X,Y may be a cyclic radical of formula (a) or (b).

2. Anisotropic compounds according to claim 1, wherein X is different from Y.

3. Anisotropic compounds according to claim 2, wherein at least one X, Y, $R^1$ or $R^2$ is an alkyl, alkoxy, or monoalkylamino group.

4. Anisotropic compounds according to claim 3, wherein the alkyl portion of said alkyl, alkoxy, or monoalkylamino group is a straight chain alkyl radical.

5. Anisotropic compounds according to claim 4, wherein said alkyl radical contains 3 to 8 C-atoms.

6. Anisotropic compounds according to claim 1, wherein X is a cyclic radical of said formula (1a) or (1b).

7. An anisotropic compound according to claim 6, having the formula:

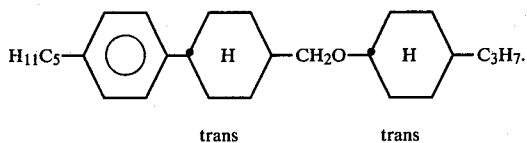

8. Anisotropic compounds according to claim 1, wherein Y is a cyclic radical of said formula (1a) or (1b).

9. An anisotropic compound according to claim 8, having the formula:

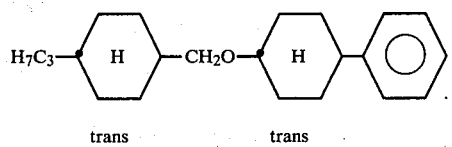

10. A liquid crystal mixture, containing at least one anisotropic compound according to claim 1.

11. A liquid crystal mixture, containing at least one anisotropic compound according to claim 2.

12. A liquid crystal mixture, containing at least one anisotropic compound according to claim 5.

13. A liquid crystal mixture, containing at least one anisotropic compound according to claim 6.

14. A liquid crystal mixture, containing at least one anisotropic compound according to claim 8.

* * * * *